POLYMERIZABLE ESTERS

This is a continuation of application Ser. No. 718,487, filed Aug. 30, 1976, now abandoned, which is a divisional of application Ser. No. 548,702, filed Feb. 10, 1975, now U.S. Pat. No. 3,996,121, which issued on Dec. 7, 1976.

This invention relates to esters which polymerise on exposure to actinic radiation, to methods of polymerising such esters by means of actinic radiation and of coating a surface with such esters, to supports bearing thereon such an ester in the polymerisable state, and to supports bearing thereon an ester polymerised by means of actinic radiation.

Substances capable of becoming polymerised on exposure to actinic radiation are used in, for example, the preparation of printing plates for offset printing and of printed circuits, and for coating metals, such as in the manufacture of cans. There are various drawbacks in the substances presently available which may be polymerised by exposure to actinic radiation. Some are so unstable that they must be applied to a substrate only immediately prior to exposing them to actinic radiation. Others are relatively insensitive and need lengthy exposure to actinic radiation in order to become sufficiently polymerised. Others, after being polymerised, are not resistant to etching baths used in subsequent processes. Most previously known substances which polymerise on exposure to actinic radiation are used with a sensitiser such as Michler's ketone (bis(p-dimethylamino)-benzophenone) or benzoin and its alkyl ethers to shorten the exposure time required for polymerisation. However, the sensitiser alters the electrical properties of the polymer, and may volatilise on being heated under pressure so making it unsuitable for use in multilayer laminates; in the preparation of these, therefore, the polymer is removed after the metal etching process has taken place, which removal adds to the cost of the laminates and may cause damage to the surface of the metal. Almost all the polymerisable compounds hitherto employed have to be isolated or purified after manufacture before they are suitable for use.

We have now found that these drawbacks can be at least substantially overcome by the use of certain novel esters.

The aforesaid esters may be prepared by the addition reaction of a polyepoxide having, per average molecule, at least three 2,3-epoxypropyl groups directly attached to oxygen, nitrogen, or sulphur atoms with a dihydric phenol of specified formula in order to advance the polyepoxide, that is, to link two or more molecules of the polyepoxide and so increase the number of epoxide groups per average molecule, and then subjecting the advanced polyepoxide to a second addition reaction with certain olefinically-unsaturated monocarboxylic acids.

If desired, a mixture of such polyepoxides may be used.

The polyepoxides employed may be represented by the formula

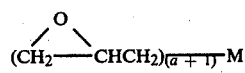    I where
a is an integer of at least two, and

M represents the residue of a polyglycidyl compound after removal of (a + 1) glycidyl groups directly attached to oxygen, nitrogen, or sulphur atoms, the said residue being linked through oxygen, nitrogen or sulphur atoms to the indicated glycidyl group.

The dihydric phenol employed is of the formula

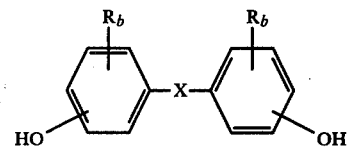    II or

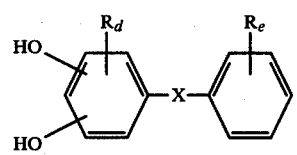    III where
each R represents a halogen atom, an alkyl, cycloalkyl, alkenyl, alkoxy, carbalkoxy, or nitro group, or a carboxyl or sulphonic acid or phosphonic acid group in the form of a salt, the said alkyl, cycloalkyl, alkenyl, alkoxy, and carbalkoxy groups preferably containing a maximum of 9 carbon atoms, each b represents zero or an integer of 1 to 4,
d represents zero or an integer of 1 to 3,
e represents zero or an integer of 1 to 5, and
X represents a chain of carbon atoms containing in that chain a grouping of formula

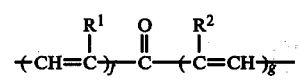    IV or

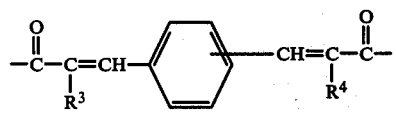    V or

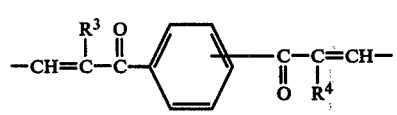    VI $R^1$ and $R^2$ individually are each a hydrogen atom, an alkyl group of 1 to 4 carbon atoms or a phenyl group, or $R^1$ and $R^2$ conjointly denote a polymethylene chain of 2 to 4 methylene groups, $R^3$ and $R^4$ are each a hydrogen atom, an alkyl group of 1 to 4 carbon atoms, or a phenyl group, and f and g are each zero, 1, or 2, with the proviso that they are not both zero.

The olefinically-unsaturated monocarboxylic acids are of the formula YH, where Y represents an olefinic acyloxy group of formula

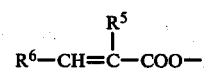    VII wherein
$R^5$ represents a hydrogen, chlorine or bromine atom, a cyano group, or an alkyl group of up to 4 carbon atoms, such as a methyl group, and

United States Patent [19]

Green et al.

[11] 4,161,588

[45] Jul. 17, 1979

[54] POLYMERIZABLE ESTERS

[75] Inventors: George E. Green, Cherry Hinton, England; Ewald Losert, Birsfelden, Switzerland

[73] Assignee: Ciba-Geigy Corporation, Ardsley, N.Y.

[21] Appl. No.: 866,321

[22] Filed: Jan. 3, 1978

Related U.S. Application Data

[60] Continuation of Ser. No. 718,487, Aug. 30, 1976, abandoned, which is a division of Ser. No. 548,702, Feb. 10, 1975, Pat. No. 3,996,121.

[30] Foreign Application Priority Data

Feb. 22, 1974 [GB] United Kingdom ............... 8105/74

[51] Int. Cl.$^2$ ........................................... C07D 303/02
[52] U.S. Cl. ............................ 542/432; 260/348.59; 542/433; 542/438; 542/439; 204/159.23; 260/348.64
[58] Field of Search ............... 260/384 A, 836, 837 R, 260/829, 47 EP, 47 UA, 47 UP; 542/432, 433, 438, 439

[56] References Cited

U.S. PATENT DOCUMENTS

| 3,301,743 | 1/1967 | Fekete et al. ..................... 260/836 |
| 3,641,064 | 2/1972 | Heer et al. ..................... 260/348 A |
| 3,644,431 | 2/1972 | Heer et al. ..................... 260/348 A |
| 3,804,862 | 4/1974 | Fetscheir et al. ............... 260/348 A |
| 3,808,114 | 4/1974 | Tsuchihara et al. ............ 204/159.15 |
| 3,882,187 | 5/1975 | Takiyama et al. ................ 260/835 |

*Primary Examiner*—Arthur P. Demers
*Attorney, Agent, or Firm*—Joseph F. DiPrima

[57] ABSTRACT

The products, which are based on polyepoxides, polymerize on exposure to actinic radiation and are useful in the preparation of printing plates for offset printing and of printed circuits, particularly multilayer circuits. They are formed by coupling two molecules of a polyepoxide by means of a dihydric phenol which contains a chalcone or chalcone-like grouping, such as 1,3-bis(p-hydroxyphenyl)prop-1-en-3-one or 1,5-bis(p-hydroxyphenyl)penta-1,4-dien-3-one, so sensitizing the material to the radiation, and then, to achieve polymerizability, ring-opening at least some of the residual epoxide groups so as to incorporate olefinic acyloxy groups ($R^6CH=C(R^5)COO-$), such as sorboyl groups.

7 Claims, No Drawings sulphur atoms, and we therefore prefer to use less than the stoichiometric amount of the acid of formula YH calculated on the epoxide group content of the advanced polyepoxide. Conveniently, from 0.5 to 0.98 equivalent of the acid is used per epoxide group of the advanced polyepoxide.

Those esters in which the residues M are linked through oxygen atoms to the indicated 2-hydroxypropylene groups may also be prepared by the addition reaction of a diglycidyl ether of formula

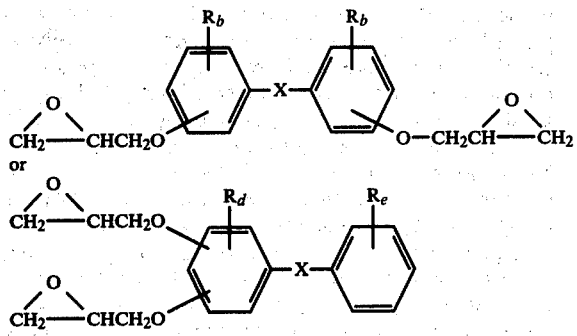

with both
(i) a compound having at least three carboxylic acid, phenolic hydroxyl or alcoholic hydroxyl groups, and
(ii) a monoglycidyl ester of formula

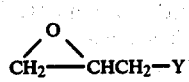 XVII the compound (i) converting the indicated glycidyl ether groups of the said diglycidyl ether and the glycidyl ester group of the compound (ii) into 2-hydroxypropylene groups. These reactions, too, may take place simultaneously or sequentially in solution, preferably in the presence of a catalyst and of a free radical inhibitor as described above.

It is important in these reactions that only sufficient of the dihydric phenol of formula II or III, or of the diglycidyl ether XV or XVI, is added to bring about advancement: as those skilled in the art of advancing epoxide resins will understand, too large a quantity could cause curing of the mixture, i.e., formation of an insoluble, infusible, cross-linked product. In general, from 0.2 to 0.67 phenolic hydroxyl equivalent of the dihydric phenol of formula II or III is used per 2,3-epoxypropyl group attached to oxygen, nitrogen, or sulphur in the aforesaid polyepoxide. Conversely, preferably from 0.2 to 0.67 epoxide equivalent of the diglycidyl ether of formula XV or XVI is used per active hydrogen equivalent of the compound containing at least three carboxylic acid, phenolic hydroxyl, or alcoholic hydroxyl groups, and from 0.5 to 1 epoxide equivalent of the monoglycidyl ester of formula XVII per active hydrogen equivalent in the reaction product of the aforesaid diglycidyl ether with the aforesaid compound containing at least three carboxylic acid, phenolic hydroxyl, or alcoholic hydroxyl groups.

As examples of suitable polyepoxides may be mentioned polyglycidyl esters obtainable by reaction of a compound containing three or more free carboxyl groups per molecule with epichlorohydrin or glycerol dichlorohydrin in the presence of an alkali. Such polyglycidyl esters may be derived from aliphatic polycarboxylic acids, from cycloaliphatic polycarboxylic acids, and from aromatic polycarboxylic acids. There may also be used homopolymers of glycidyl esters of ethylenically unsaturated acids and copolymers of such glycidyl esters with a second, ethylenically unsaturated compound. Suitable homopolymers and copolymers include poly(glycidyl acrylate), poly(glycidyl methacrylate) and copolymers of an α-mono-olefin such as styrene or methyl methacrylate with glycidyl acrylate or glycidyl methacrylate.

Further examples of suitable polyepoxides are poly-

XV

XVI glycidyl ethers obtainable by reaction of a compound containing at least three free alcoholic hydroxy or phenolic hydroxy groups per molecule with epichlorohydrin or glycerol dichlorohydrin under alkaline conditions or, alternatively, in the presence of an acidic catalyst and subsequent treatment with alkali. These glycidyl ethers may be derived from acyclic alcohols, from alcohols having aromatic nuclei, and from polynuclear phenols such as novolaks.

Poly(N-glycidyl) compounds which may be used include those obtained by dehydrochlorinating the reaction product of epichlorohydrin with an amine containing at least three amino-hydrogen atoms, such as bis(p-aminophenyl)methane and bis(p-aminophenyl)sulphone, and also triglycidyl isocyanurate and tri-N-glycidyl derivatives of compounds containing hydantoin rings.

Examples of poly(S-glycidyl) compounds are the tris(S-glycidyl) derivatives, described in our United Kingdom Patent Specification No. 1,352,527, of cyclododecanetrithiols prepared from cyclododeca-1,5,9-triene.

Polyepoxides having terminal 1,2-epoxide groups attached to different kinds of hetero atoms may also be employed, e.g., the N,N,O-triglycidyl derivative of p-aminophenol.

The preferred polyepoxides are polyglycidyl ethers of phenols, especially of a phenol-formaldehyde or cresol-formaldehyde novolak or of 1,1,2,2-tetrakis(p-hydroxyphenyl)ethane, and of phenolic alcohols (the ethers bearing glycidyl groups on phenolic and alcoholic hydroxyl groups) such as those of the formula

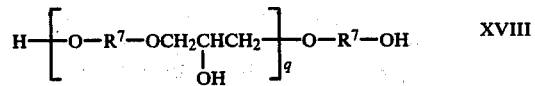 XVIII where
R⁷ is the residue of a dihydric phenol after removal of two phenolic —OH groups, and preferably denotes

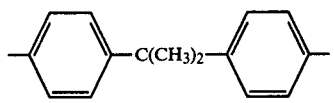

XIX and q is an integer of average value at least 1 and at most 50.

Dihydric phenols of formulae II and III are obtainable by condensation of an aromatic monoaldehyde, such as benzaldehyde, o-, m-, or p-hydroxybenzaldehyde or o-, m-, or p-hydroxyphenylacetaldehyde, or an aromatic dialdehyde, such as terephthaldehyde, with a ketone, such as o-, m-, or p-hydroxyacetophenone, o-, m-, or p-hydroxyphenyl ethyl ketone, acetone, cyclohexanone, cyclopentanone, cycloheptanone, and 2,4-dihydroxyphenyl methyl ketone. The reactants and their molecular ratios must be selected to give two, and substantially only two, hydroxy groups in the resultant product. Condensation may be effected in aqueous solution in the presence of a base at ambient or elevated temperature.

Particularly preferred phenols of formula II and III are 1,4-bis(p-hydroxy-benzoylvinyl)benzene, 1,5-bis(p-hydroxyphenyl)penta-1,4-dien-3-one, and 1,3-bis(p-hydroxyphenyl)prop-1-en-3-one; therefore most preferably represents formula IV, with $R^3$ and $R^4$ both denoting hydrogen, and the benzene ring being so substituted in the para position, or formula IV, with $R^1$ and $R^2$ both denoting hydrogen, f denoting 1, and g denoting zero or 1.

If desired, part of the dihydric phenol of formula II or III may be replaced with a phenol not having the group X and containing two, but not more than two, phenolic hydroxyl groups. Examples of such phenols are hydroquinone and 2,2-bis(p-hydroxyphenyl)propane. Preferably, however, the unit of formula IX or X constitutes at least 0.1% and preferably 1 to 15%, by weight of the polymerisable ester which is to be polymerised by irradiation.

Of the compounds, having on average at least three carboxylic acid or phenolic or alcoholic hydroxy groups, which may be treated with compounds of formula XV or XVI and XVII to give the polymerisable esters, phenolic novolaks (especially phenol-formaldehyde and cresol-formaldehyde novolaks) and 1,1,2,2-tetra(p-hydroxyphenyl)ethane are preferred.

Glycidyl ethers of formulae XV and XVI and glycidyl esters of formula XVII are prepared by known methods from the corresponding hydroxy compounds of formula II and III or acids of formula Y-H by treatment with epichlorohydrin or glycerol dichlorohydrin under alkaline conditions or, alternatively, in the presence of an acidic catalyst and subsequent treatment with alkali (see for example our German Offenlegungsschrift No. 2342407).

As already indicated, it is preferred to employ an ester containing 1,2-epoxide groups. The irradiated ester may then be cross-linked through reaction with a polycarboxylic acid anhydride or other heat-curing agent for epoxide resins, especially dicyandiamide. (Epoxide resins are substances containing on average more than one 1,2-epoxide group per molecule.) Such additional cross-linking often enhances the adhesion of the polymerised composition to the support.

In polymerising the esters of this invention, actinic radiation of wavelength 200 to 600 nm is preferably used.

As prepared, the esters may contain small quantities of a hydroquinone or other free-radical inhibitor added to prevent free radical polymerisation taking place during preparation of the ester. Such inhibitors are usually not deleterious since they maintain the stability of the ester during storage but do not prevent polymerisation on exposure to actinic radiation.

The esters used in the process of this invention are of particular value in the production of printing plates and printed circuits, especially multilayer printed circuits which can be prepared without removal of the photopolymerised ester. A layer of the ester may be applied to a support by coating the support with a solution of the ester in any convenient solvent, e.g., cyclohexanone, or a mixture of toluene and acetone or of toluene and ethyl methyl ketone, and allowing or causing the solvent to evaporate; the layer may be applied by dipping, spinning, spraying, or by means of a roller.

This invention also includes a plate sensitive to actinic radiation comprising a support, which may be of, for example, paper, copper, aluminium or other metal, synthetic resin, or glass, carrying a layer of such an ester, also a support bearing upon its surface such an ester which has been polymerised by exposure to actinic radiation. It also provides a method of polymerising such an ester, which comprises subjecting a plate carrying a layer of the ester to actinic radiation, optionally imagewise as through a negative, and removing the unpolymerised portions, if any, of the ester by means of a solvent.

The coating of the ester should be applied to the support so that, upon drying, its thickness will be in the range of from about 1 to 250 μm. The thickness of the polymerisable layer is a direct function of the thickness desired in the relief image, which will depend on the subject being reproduced and particularly on the extent of the non-printing areas. The wet polymer coating may be dried by air drying or by any other known drying technique, and the polymerisable system may then be stored until required for use.

The polymerisable coatings can be insolubilised by exposure to actinic radiation through an image-bearing transparency consisting of substantially opaque and transparent areas. Suitable sources of actinic radiation include carbon arcs, mercury vapour arcs, fluorescent lamps with phosphors emitting ultra-violet light, argon and xenon glow lamps, tungsten lamps, and photographic flood lamps. Of these, mercury vapour arcs, particularly sun lamps, fluorescent sun lamps, and metal halide lamps are most suitable. The time required for the exposure of an ester will depend upon a variety of factors which include, for example, the individual ester being utilised, the thickness of the coating, the type of light source, and its distance from the coating.

Subsequent to their exposure the coatings are "developed" by being washed with a suitable liquid, such as perchloroethylene, methylene chloride, ethylene dichloride, acetone, ethyl methyl ketone, cyclohexanone, n-propanol, ethanol, toluene, benzene, ethyl acetate, and mixtures thereof, to dissolve and remove that portion of the coating which was not polymerised by exposure to actinic radiation. Liquids used for this operation must be selected with care since they should have good solvent action on the unexposed areas yet have little effect upon either the polymerised ester or the substrate.

The developing solvent should normally be allowed to remain in contact with the coating for from about 30 seconds to 3 minutes, depending upon which solvent is utilized. The developed polymer coating should next be rinsed with fresh solvent and dried.

If appropriate, for example, in the production of printed circuits where the support is of copper or of other suitable electrically-conducting metal, the exposed metal is etched in a conventional manner using ferric chloride or ammonium persulphate solutions.

The ester may, if desired, be partially polymerised before applying it to the support, in order to improve the film-forming or mechanical properties of the irradiated product. Such a partial prepolymerisation can be effected by heating: it should not, however, proceed beyond the stage at which a correctly differentiated image is obtained on the plate when the plate is exposed. The ester may also be heated after exposure to actinic radiation to enhance the degree of polymerisation.

For purposes of comparison the following experiments were carried out. Throughout this Specification, temperatures are in degrees Celsius and parts are by weight.

EXPERIMENT 1

A mixture of 50 g of an epoxy novolak resin (having an epoxide content of 5.48 equiv./kg and being a polyglycidyl ether made from a phenol-formaldehyde novolak of number average molecular weight 420, hereinafter called "Epoxy novolak I"), sorbic acid (16.7 g), 2,2-bis(p-hydroxyphenyl)propane (11.45 g), hydroquinone (0.08 g), tetramethylammonium chloride (0.25 g), and cyclohexanone (80 g) was stirred at 120° for 5 hours, by which time the epoxide content of the solution had fallen to 0.24 equiv./kg. This solution was diluted with cyclohexanone to a solids content of 25% and treated in the following manner.

A copper-clad laminate was coated with the composition and the solvent was allowed to evaporate, leaving a film about 10 μm thick. This film was irradiated through a negative with a 550 watt medium pressure mercury lamp at a distance of 450 mm. Exposure for 30 minutes was necessary. After irradiation the plate was developed for 30 seconds in cyclohexanone to leave a good relief image on the copper.

EXPERIMENT IA

When Experiment I was repeated but with the addition of the diluted solution of Michler's ketone as sensitiser (1 or 10% by weight of the polysorbate) the same quality image was obtained after only 5 minutes' irradiation.

EXPERIMENT IB

When 1,5-di-(p-hydroxyphenyl)penta-1,4-dien-3-one was added in place of Michler's ketone as sensitiser (15% by weight of the polysorbate) in Experiment IA the same quality image was obtained after 6 minutes' irradiation.

In all of the above cases shorter times gave inferior images with poorer resistance to solvents.

EXPERIMENT 2

A mixture of Epoxy novolak I (50 g), 2,2-bis(p-hydroxyphenyl)propane (11.45 g), cinnamic acid (22.1 g), hydroquinone (0.1 g), tetramethylammonium chloride (0.25 g), and cyclohexanone (84 g) was stirred at 120° for 5 hours, by which time the epoxide content was 0.27 equiv./kg.

A solution containing 25% by weight of solids was tested as in Experiment 1. A good relief image was obtained after 30 minutes' irradiation without sensitiser. When Michler's ketone (1% by weight of polycinnamate) was added, the same quality image could be obtained after only 5 minutes' irradiation.

EXPERIMENT 3

A mixture of Epoxy novolak I (50 g), 2,2-bis(p-hydroxyphenyl)propane (11.45 g), 3-(2-furyl)acrylic acid (20.6 g), hydroquinone (0.1 g), tetramethylammonium chloride (0.25 g), and cyclohexanone (82 g) was stirred at 120° for 5 hours, by which time the epoxide content was 0.28 equiv./kg.

A solution containing 25% by weight of solids of the product was tested as in Experiment 1, and a good relief image was obtained after 20 minutes' irradiation. With Michler's ketone (1% by weight of the polyfurylacrylate) added, the same quality image could be obtained after only 3 minutes' irradiation.

EXPERIMENT 4

A mixture of Epoxy novolak I (50 g) 2,2-bis(p-hydroxyphenyl)propane (11.45 g), methacrylic acid (12.8 g), hydroquinone (0.1 g), tetramethylammonium chloride (0.25 g), and cyclohexanone (75 g) was stirred at 120° for 2½ hours, by which time the epoxide content was 0.41 equiv./kg.

A solution containing 25% by weight of solids was tested as in Experiment 1, except that toluene was used as the developing solvent instead of cyclohexanone. No image could be obtained after 30 minutes' irradiation. With benzoin methyl ether (1% by weight of the polymethacrylate) added, a good relief image was obtained after 15 minutes' irradiation.

EXPERIMENT 5

A mixture of 50 g of Epoxy novolak I, sorbic acid (24 g), 2,2-bis(p-hydroxyphenyl)propane (7.4 g), hydroquinone (0.1 g), tetramethylammonium chloride (0.25 g), and cyclohexanone (80 g) was stirred at 120° for 2¾ hours, by which time the epoxide content of the solution had fallen to 0.32 equiv./kg.

Michler's ketone (1% by weight of the polysorbate) was dissolved in this solution and the composition was tested as described in Experiment 1. A good relief image was obtained after 15 minutes' irradiation and was developed in toluene. If the Michler's ketone were omitted, no image was obtained on developing with toluene, even if the irradiation time were extended to 30 minutes.

EXPERIMENT 6

A mixture of 50 g of the tetraglycidyl ether of 1,1,2,2-tetrakis(p-hydroxyphenyl)ethane (having an epoxide content of 4.55 equiv./kg), sorbic acid (19.7 g), 2,2-bis(p-hydroxyphenyl)propane (5.9 g), hydroquinone (0.1 g), tetramethylammonium chloride (0.25 g), and 2-ethoxyethyl acetate (80 g) was stirred at 120° for 4 hours, by which time the epoxide content of the mixture had fallen to 0.5 equiv./kg.

When the composition was tested as described in Experiment 1, 30 minutes' irradiation was required in order to produce a reasonable relief image that could be developed in cyclohexanone.

EXPERIMENT 7

The tetrakis(N-glycidyl) derivative of bis(p-aminophenyl)methane having an epoxide content of 7.6 equiv./kg (50 g), sorbic acid (29 g), 2,2-bis(p-hydroxyphenyl)propane (14.8 g), hydroquinone (0.1 g), tetramethylammonium chloride (0.25 g), and 2-ethoxyethyl acetate (94 g) were heated together at 120° for 4 hours, by which time the epoxide content of the mixture was negligible.

The composition was tested as described in Experiment 1. It took a minimum of 30 minutes' irradiation to give an acceptable relief image which could be developed in cyclohexanone.

EXPERIMENT 8

Experiment 1 was repeated, substituting cyclohexanone by 2-ethoxyethyl acetate with the same result.

The invention is illustrated by the following Examples.

EXAMPLE 1

Experiment 1 was repeated, using 13.5 g of 1,4-bis(p-hydroxybenzoylvinyl)benzene in place of the 2,2-bis(p-hydroxyphenyl)propane. The final epoxide content of the mixture was 0.48 equiv./kg.

When the composition was tested as described in Experiment 1, a good relief image, the same quality as that obtained in Experiment 1, was obtained after only 5 minutes' irradiation; when the composition was irradiated in the presence of Michler's ketone (1% calculated on the weight of polysorbate) as sensitiser, the time taken for an image of the same quality to be produced was the same (compare Experiment 1, where irradiation for 30 minutes was required without sensitiser and for 5 minutes with sensitiser).

EXAMPLE 2

Experiment 1 was repeated, using 13.8 g of 1,5-bis(p-hydroxyphenyl)penta-1,4-dien-3-one in place of the 2,2-bis(p-hydroxyphenyl)propane. The final epoxide content of the mixture was 0.3 equiv./kg.

When the composition was tested as in Experiment 1, a good relief image of the same quality as in Experiment 1 was obtained after 4 minutes' irradiation, and the time taken to produce an image of the same quality was not reduced by the addition of Michler's ketone (1% based on weight of polysorbate).

EXAMPLE 3

Experiment 2 was repeated, using 13.3 g of 1,5-bis(p-hydroxyphenyl)penta-1,4-dien-3-one in place of the 2,2-bis(p-hydroxyphenyl)propane. The final epoxide content of the solution was 0.32 equiv./kg.

When this product was tested as in Experiment 2, a good relief image, having the same quality as that obtained in Experiment 2, was obtained after 4 minutes' irradiation. The time taken to produce an image of the same quality could not be reduced by the addition of Michler's ketone as sensitiser (1% by weight of the polycinnamate).

EXAMPLE 4

Experiment 3 was repeated, using 13.3 g of 1,5-bis(p-hydroxyphenyl)penta-1,4-dien-3-one in place of the 2,2-bis(p-hydroxyphenyl)propane. The final epoxide content of the mixture was 0.35 equiv./kg.

When this product was tested as in Experiment 3, a good relief image, with the same quality as that obtained in Experiment 3, was obtained after 3 minutes' irradiation. The time taken to produce an image of the same quality was not reduced by the addition of Michler's ketone (1% by weight of the polyfurylacrylate) as sensitiser.

EXAMPLE 5

Experiment 4 was repeated, using 13.3 g of 1,5-bis(p-hydroxyphenyl)penta-1,4-dien-3-one in place of the 2,2-bis(p-hydroxyphenyl)propane. The final epoxide content of the mixture was 0.2 equiv./kg.

When this product was tested as in Experiment 4, a good relief image was obtained after 8 minutes' irradiation. The time taken to produce an image of the same quality could not be reduced by addition of benzoin methyl ether (1% by weight of the polymethacrylate) as sensitiser.

EXAMPLE 6

Experiment 5 was repeated, using 4.6 g of 1,5-bis(p-hydroxyphenyl)penta-1,4-dien-3-one and 3.4 g of 2,2-bis(p-hydroxyphenyl)propane in place of the 2,2-bis(p-hydroxyphenyl)propane.

When the composition was tested as described in Experiment 5 but omitting the Michler's ketone, a good relief image, the same quality as that obtained in Experiment 5 — when Michler's ketone was used — was obtained after 10 minutes' irradiation.

EXAMPLE 7

Experiment 6 was repeated, using 6.99 g of 1,5-bis(p-hydroxyphenyl)penta-1,4-dien-3-one in place of the 2,2-bis(p-hydroxyphenyl)propane. The final epoxide content of the mixture was 0.34 equiv./kg.

When the composition was tested as in Experiment 1, a good relief image was obtained after 5 minutes' irradiation that could be developed in cyclohexanone (c.f. Experiment 6, where 30 minutes' irradiation was required).

In this and Examples 8 and 9 the uncoated copper areas were then etched with a 40% w/v aqueous solution of ferric chloride.

EXAMPLE 8

Experiment 7 was repeated, using a mixture of 9.0 g of 1,5-bis(p-hydroxyphenyl)penta-1,4-dien-3-one and 7.0 g of 2,2-bis(p-hydroxyphenyl)propane in place of the 14.8 g of 2,2-bis(p-hydroxyphenyl)propane. The final epoxide content of the mixture was negligible.

When this composition was tested as in Experiment 7, a good relief image, with a better quality than that obtained in Experiment 7, was obtained after 15 minutes' irradiation.

EXAMPLE 9

Experiment 8 was repeated, using 15.3 g of 4,4'-dihydroxychalcone (i.e., 1,3-bis(p-hydroxyphenyl)prop-1-en-3-one) in place of the 2,2-bis(p-hydroxyphenyl)propane.

When this composition was tested as described in Experiment 8, a good relief image was obtained after 15 minutes' irradiation.

EXAMPLE 10

To 20 g of the product from Example I was added 0.1 g of dicyandiamide. A copper-clad laminate was coated with this composition and the solvent was allowed to evaporate, leaving a film about 20 μm thick. After irradiation for 5 minutes and development in cyclohexanone the plate was heated at 180° for 30 minutes.

What we claim is:

1. An ester which polymerizes on exposure to actinic radiation which comprises the product obtained by reacting (1) an advancement product of one equivalent of a polyepoxide having per average molecule at least three 2,3-epoxypropyl groups directly attached to oxygen, nitrogen or sulfur atoms with 0.2 to 0.67 equivalents of a dihydric phenol of the formula

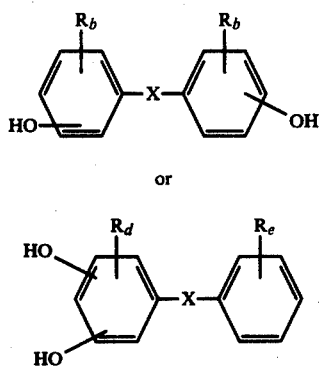

wherein
each R represents halogen, alkyl, cycloalkyl, alkenyl, alkoxy, or carbalkoxy group each containing up to 9 carbon atoms, nitro, carboxyl, sulphonic acid or phosphonic acid group in the form of a salt,
each b represents zero or an integer of 1 to 4,
d represents zero or an integer of 1 to 3,
e represents zero or an integer of 1 to 5, and
x represents a grouping of the formula

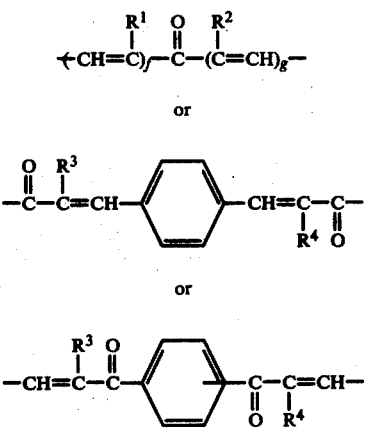

wherein
$R^1$ and $R^2$ individually are each a hydrogen atom, an alkyl group of 1 to 4 carbon atoms, or a phenyl group, or conjointly denote a polymethylene chain of 2 to 4 methylene groups, $R^3$ and $R^4$ are each a hydrogen atom, an alkyl group of 1 to 4 carbon atoms, or a phenyl group, and
f and g are each zero, 1, or 2, with the proviso that they are not both zero, and (ii) 0.5 to 0.98 equivalents of an olefinically unsaturated monocarboxylic acid of the formula YH per equivalent of (i) wherein
Y represents an olefinic acyloxy group of formula

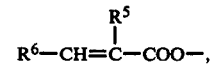

wherein
$R^5$ represents a hydrogen, chlorine, or bromine atom, a cyano group, or a alkyl group of up to 4 carbon atoms, and
$R^6$ represents a hydrogen atom or an aliphatic, aromatic, or araliphatic group each group having up to 12 carbon atoms, or a 2-furyl group.

2. Esters according to claim 1, in which $R^6$ represents a group having olefinic unsaturation or aromaticity in conjugation with the indicated olefinic bond.

3. Esters according to claim 2, in which Y represents a sorboyloxy, cinnamoyloxy, 3-(2-furyl)acryloyloxy, methacryloyloxy, or acryloyloxy group.

4. Esters according to claim 1, in which X represents

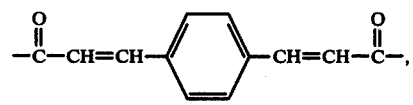

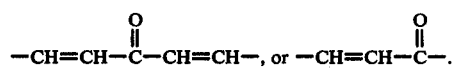

5. Esters according to claim 1, in which units of formula

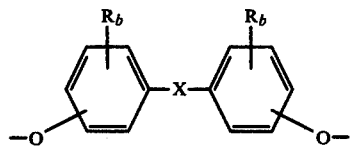

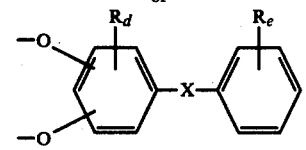

constitute at least 0.1% by weight of the polymerisable ester.

6. Esters according to claim 1, in which the polyepoxide employed as starting material is a polyglycidyl ether of a phenol, or the ether bearing glycidyl groups on phenolic and alcoholic hydroxyl groups, of a phenolic alcohol.

7. Esters according to claim 1, that contain residual 1,2-epoxide groups.

* * * * *